United States Patent [19]

Iwao et al.

[11] Patent Number: 4,547,513
[45] Date of Patent: Oct. 15, 1985

[54] 2-ARYLBENZOTHIAZOLINE DERIVATIVES AND THEIR USE IN TREATING ANGINA CORDIS

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 679,466

[22] Filed: Dec. 7, 1984

[30] Foreign Application Priority Data

Dec. 27, 1983 [JP] Japan ................. 58-251934

[51] Int. Cl.[4] ......................... C07D 417/02
[52] U.S. Cl. ..................... 514/321; 546/198
[58] Field of Search ............ 546/198; 514/327

[56] References Cited

FOREIGN PATENT DOCUMENTS

WO83/00865  3/1983  PCT Int'l Appl. ............. 546/198

Primary Examiner—Henry R. Jiles
Assistant Examiner—Patricia Ann Bucci

Attorney, Agent, or Firm—Frishauf, Holtz, Goodman & Woodward

[57] ABSTRACT

This invention relates to novel benzothiazoline derivatives of the formula [I] and salts thereof,

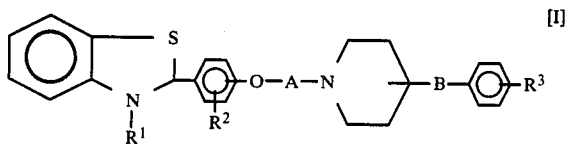

wherein
$R^1$ is formyl or lower alkanoyl;
$R^2$ is hydrogen, lower alkyl, lower alkoxy or nitro;
$R^3$ is hydrogen, lower alkyl, lower alkoxy or halogen;
A is lower alkylene;
B is $-CO-(CH_2)_m-$ or $-CH(OH)-$;
m is 0 or 1; and
when m is 0, $R^3$ is not hydrogen.

The compounds of this invention are useful for treatment of cardiovascular diseases.

14 Claims, No Drawings

2-ARYLBENZOTHIAZOLINE DERIVATIVES AND THEIR USE IN TREATING ANGINA CORDIS

DETAILED DESCRIPTION OF THE INVENTION

This invention relates to the compounds of the formula [I] and salts thereof,

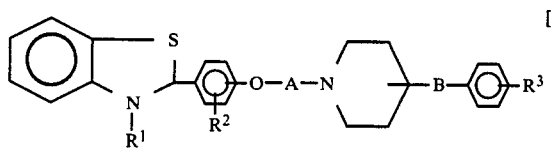

[I]

wherein
$R^1$ is formyl or lower alkanoyl;
$R^2$ is hydrogen, lower alkyl, lower alkoxy or nitro;
$R^3$ is hydrogen, lower alkyl, lower alkoxy or halogen;
A is lower alkylene;
B is —CO—$(CH_2)_m$— or —CH(OH)—;
m is 0 to 1; and
when m is 0, $R^3$ is not hydrogen.

The term "lower alkanoyl" is intended to designate $C_2$–$C_6$ alkanoyl exemplified by acetyl, propanoyl and hexanoyl.

The term "halogen" is intended to designate fluorine, chlorine or bromine.

The term "lower alkyl" is intended to designate $C_1$–$C_6$ alkyl exemplified by methyl, ethyl, propyl, butyl and hexyl.

The term "lower alkoxy" is intended to designate $C_1$–$C_6$ alkoxy exemplified by methoxy, ethoxy, propoxy and hexyloxy.

The term "lower alkylene" is intended to designate straight or branched $C_1$–$C_6$ alkylene exemplified by methylene, ethylene, propylene, butylene and hexylene.

The compounds of this invention are novel 2-phenylbenzothiazoline derivatives which are useful for treatment of cardiovascular diseases. The compounds of this invention have a specific structure where the 2-position of the benzothiazoline ring is substituted by a phenyl group having a heterocycle at the side chain.

Recently, we synthesized 2-phenylbenzothiazoline derivatives and disclosed them in GB Pat. No. 2115815 published on Sept. 14, 1983.

We continuously studied the derivatives of 2-phenylbenzothiazoline in order to find more useful compounds.

As the result of our precise examination, we found novel, very useful 2-phenylbenzothiazoline derivatives represented by the formula [I].

The compounds of this invention possess superior platelet anti-aggregation effect and calcium antagonization. Iihibitors of platelet aggregation and calcium antagonists are used as therapeutic agents for cardiovascular diseases such as angina cordis, arrhythmia, thrombosis, etc., so the compounds of this invention are useful for treatment of cardiovascular diseases.

The pharmacological tests prove the superior effect of the compounds of this invention.

The compounds of this invention can be prepared by the reaction of halide of the formula [II] with amine derivative of the formula [III].

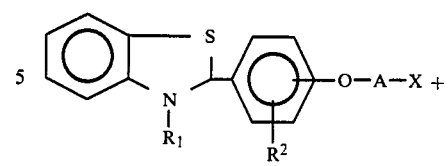

[II]

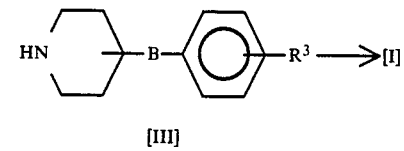

[III]

wherein X is halogen.

The above reaction needs no specific conditions, and known methods which are generally used for a reaction of amine derivatives with halides can be used. For example, heating of a mixture of amine derivative and halide, a reaction of amine derivative with halide in a presence of base such as triethylamine in an organic solvent.

The compounds of the formula [II] can be prepared according to the disclosure of GB Pat. No. 2115815.

The compounds of the formula [III] can be prepared by known methods which are summarized as follows.

(a)

CH₃CO—N⟩—COCl +

⟨◯⟩—R³ —Friedel-Crafts reaction→

CH₃CO—N⟩—CO—⟨◯⟩—R³ —hydrolysis→

HN⟩—CO—⟨◯⟩—R³

(b)

CH₃CO—N⟩—COCl + ⟨N◯⟩—SH →

CH₃CO—N⟩—COS—⟨N◯⟩ —R³—⟨◯⟩—CH₂MgCl→

CH₃CO—N⟩—COCH₂—⟨◯⟩—R³ —hydrolysis→

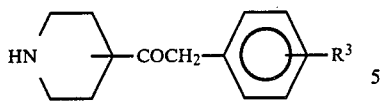

The compounds of the formula [III], wherein B is —CH(OH)—, can be prepared by reduction of the corresponding carbonyl compound.

The compounds [I] of this invention can be converted into acid salts. Said salts are obtained by usual methods using inorganic or organic acids. Examples of pharmaceutically acceptable salts of the compounds are hydrochloric acid salt, sulfuric acid salt, phosphoric acid salt, lactic acid salt, maleic acid salt, fumaric acid salt, oxalic acid salt, succinic acid salt, citric acid salt, methanesulfonic acid salt, p-toluenesulfonic acid salt, etc.

The compounds of this invention have stereoisomers because of the existence of one or more asymmetric carbon atoms, and these isomers are included in this invention.

Examples are shown below.

The assignments of the NMR spectra are made according to the numbers of the formula [IV] and aromatic protons, not assigned, are shown as aromatic H. When $R^2$ or $R^3$ of the formula [I] is methoxy group, the former is shown as —OC$\underline{H}_3$(P) and the latter is —OC$\underline{H}_3$(A).

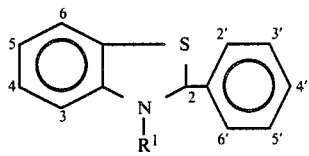

[IV]

EXAMPLE 1

3-Acetyl-2-[5-methoxy-2-[4-[4-(4-methoxybenzoyl)-1-piperidyl]butoxy]phenyl]benzothiazoline oxalate (compound 1)

A mixture of 3-acetyl-2-[2-(4-chlorobutoxy)-5-methoxyphenyl]benzothiazoline (1.60 g) and 4-(4-methoxybenzoyl)piperidine (1.78 g) is stirred for 2 hours at 110°–120° C. After cooling to room temperature, the mixture is dissolved in chloroform (30 ml). The solution is washed with N hydrochloric acid, N sodium hydroxide solution and then saturated sodium chloride solution. The solution is dried over anhydrous magnesium sulfate and concentrated in vacuo. To the oily residue, a solution of oxalic acid (0.36 g) in methanol (5 ml) is added to give 1.21 g (45%) of the titled compound.

mp 97°–103° C. (methanol–acetonitrile)
IR (KBr, cm$^{-1}$): 1664, 1597, 1465, 1377, 1276
NMR (DMSO-d$_6$, δ): 1.50–2.36

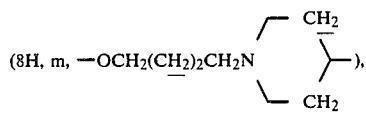

2.22 (3H, s, —COC$\underline{H}_3$), 2.73–3.85

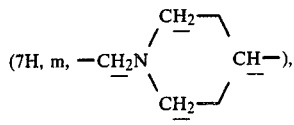

3.62 (3H, s, —OC$\underline{H}_3$(P) ), 3.88 (3H, s, —OC$\underline{H}_3$(A) ), 3.92–4.32 (2H, m, -OC$\underline{H}_2$-), 6.36–6.73 (3H, m, $\overline{C}_{6'-H}$ and —CO$_2\underline{H}\times 2$), 6.73–7.39 (8H, C$_2$-H and aromatic H), 7.73–8.22

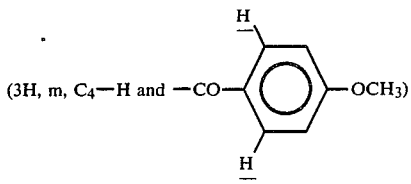

The following compound was prepared by the similar method as in Example 1.

2-[2-[4-[4-(4-fluorobenzoyl)-1-piperidyl]butoxy]-5-methoxyphenyl]-3-formylbenzothiazoline fumarate (compound 2)

Yield 45%
mp 160°–161° C. (dec.), (methanol-acetonitrile) IR (KBr, cm$^{-1}$): 1712, 1671, 1592, 1577, 1497, 1470, 1353, 1274, 1212, 1155, 1033, 744 NMR (DMSO-d$_6$, δ): 1.27–2.13

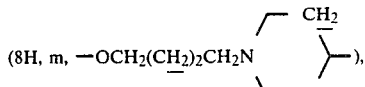

2.30–3.50

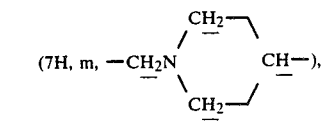

3.58 (3H, s, —OC$\underline{H}_3$(P) ), 3.80–4.27 (2H, m, —OC$\underline{H}_2$-), 6.33–8.20 (12H, m, C$_2$-H and aromatic H), 6.53

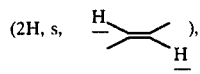

8.23–8.67 (2H, br, —CO$_2\underline{H}\times 2$), 8.47 and 8.93 (1H, each s, —C$\underline{H}$O)

EXAMPLE 2

3-Acetyl-2-(5-methoxy-2-[4-[4-(4-methylbenzoyl)-1-piperidyl]butoxy]phenyl]benzothiazoline maleate (compound 3)

A mixture of 3-acetyl 2-]2-(4-bromobutoxy)-5-methoxyphenyl]-benzothiazoline (1.31 g) and 4-(4-methylbenzoyl)piperidine (1.22 g) is stirred for one hour at 80°–90° C. After cooling to room temperature, the reaction procedure is followed by the similar procedure as in Example 1 to give 1.01 g (50%) of the titled compound.

mp (175°–178° C.
IR (KBr, cm$^{-1}$): 1671, 1604, 1577, 1493, 1465, 1379, 1275, 1208
NMR (DMSO-d$_6$), δ): 1.65–2.36

(8H, m, —OCH$_2$(CH$_2$)$_2$CH$_2$N⟨CH$_2$-CH$_2$⟩CH-CH$_2$), 2.27 (3H, s, —COCH$_3$), 2.42

(3H, s, —⟨Ph⟩—CH$_3$), 2.87–4.03

(7H, m, —CH$_2$N⟨CH$_2$-CH$_2$⟩CH—CO—), 3.67 (3H, s, -OCH$_3$(P)),
3.97–4.35 (2H, m, —OCH$_2$), 6.12

(2H, s, H—⟩=⟨—H ), 6.46 (2H, d, J=2.4 Hz, C$_6'$-H), 6.65–7.40 (5H, m, aromatic H), 6.97 (1H, s, C$_2$-H), 7.31

(2H, d, J=8.0 Hz, —⟨Ph⟩—CH$_3$), 7.76–8.07 (1H, m, C$_4$-H), 7.88

(2H, d, J=8.0 Hz, —CO—⟨Ph⟩—CH$_3$)

The following compounds were prepared by the similar method as in Example 2.

3-Acetyl-2-[2-[4-[4-(4-chlorobenzoyl)-1-piperidyl]-butoxy]-5-methoxyphenyl]benzothiazoline maleate (compound 4)
Yield 90%
mp 177.5°–179.5° C.
IR (KBr, cm$^{-1}$): 1671, 1578, 1498, 1465, 1377, 1278, 1208 NMR (DMSO-d$_6$, δ): 1.66–2.32

(8H, m, —OCH$_2$(CH$_2$)$_2$CH$_2$N⟨CH$_2$-CH$_2$⟩), 2.23 (3, s, —COCH$_3$), 2.75–4.05

(7H, m, —CH$_2$N⟨CH$_2$-CH$_2$⟩CH—), 3.53 (3H, s, —OCH$_3$(P)), 4.06 (2H, m, —OCH$_2$-), 6.04

(2H, s, H—⟩=⟨—H ), 6.45 (1H, d, J=3.0Hz, C$_6'$-H), 6.67–7.38 (5H, m, aromatic H), 6.93 (1H, s, C$_2$-H), 7.45

(2H, d, J=8.5 Hz, —CO—⟨Ph⟩—Cl), 7.70–8.19 (1H, m, C$_4$-H), 7.97

(2H, d, J=8.5 Hz, —CO—⟨Ph⟩—Cl)

3-Acetyl-2-[2-[4-[4-(α-hydroxybenzyl)-1-piperidyl]-butoxy]5-methoxyphenyl]benzothiazoline maleate (compound 5)
Yield 45%
mp 184°–188° C. (methanol-acetonitrile)
IR (KBr, cm$^{-1}$): 3370, 1638, 1571, 1487, 1476, 1457
NMR (DMSO-d$_6$, δ): 0.83–2.06

(9H, m, OCH$_2$(CH$_2$)$_2$CH$_2$N⟨CH$_2$-CH$_2$⟩CH—), 2.20 (3H, s, —COCH$_3$), 2.55–3.47

(6H, m, —CH$_2$N⟨CH$_2$-CH$_2$⟩), 3.54 (3H, s, —OCH$_3$(P)), 3.80–4.20 (2H, m, —OCH$_2$—), 4.20–4.50 (1H, m, —CH(OH)—), 4.83–5.73 (1H, br, —OH), 5.97

(2H, s, H—⟩=⟨—H ), 6,35–7.47 (12H, m, C$_2$—H and aromatic H), 7.60–8.10 (1H m, C$_4$-H)

EXAMPLE 3

3Acetyl-2-8 2-[4-[4-(4-fluorobenzoyl)-1-piperidyl]-butoxy]-5-methoxyphenyl]benzothiazoline maleate (compound 6)

To a solution of 3-acetyl-2[-2-(4-bromobutoxy)-5-methoxyphenyl]benzothiazoline (1.53 g) and 4-(4-fluorobenzoyl)piperidine (0.73 g) in ethanol (4 ml), triethylamine (0.35 g ) is added and the mixture is refluxed for 1.5 hours. After cooling to room temperature, the mixture is dissolved in chloroform (20 ml). The solution is washed with N hydrochloric acid, water, saturated sodium hydrogen carbonate solution and then saturated sodium chloride solution. The organic layer is dried over anhydrous magnesium sulfate and concentrated in vacuo. The oily residue is purified by silica gel column chromatography. The oily product (1.28 g) is dissolved in ethyl acetate (5 ml). A solution of maleic acid (0.26 g) in ethyl acetate (5 ml) is added to the solution to give 1.31 g (55%) of the titled compound.

mp 146°–149° C. (ethyl acetate-ethanol)

IR (KBr, cm$^{-1}$): 1671, 1594, 1494, 1462, 1375, 1348, 1274, 1232, 1208 NMR (DMSO-d$_6$, δ): 1.43–2.40

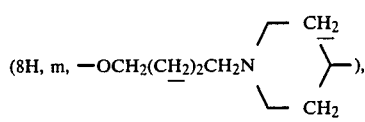

2.23 (3H, s, —COCH$_3$), 2.77–3.87

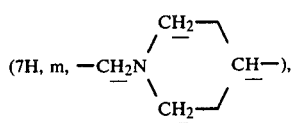

3.57 (3H, s, —OCH$_3$(P) ), 3.87–4.36 (2H, m, —OCH$_2$-), 6.03

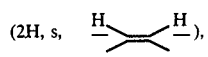

6.43 (1H, d, J=2.5 Hz, C$_6$'-H), 6.60–7.22 (7H, m, aromatic H), 7.19 (1H, s, C$_2$-H),

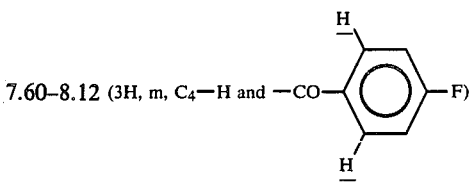

7.60–8.12 (3H, m, C$_4$—H and —CO

The following compound was prepared by the similar method as in Example 3.

3-Acetyl-2-[2-[4-(4-benzylcarbonyl-1piperidyl)butoxy]-5-methoxyphenyl]benzothiazoline maleate (compound 7)

Yield 55% mp 152°–154° C. (methanol)

IR (KBr, cm$^{-1}$): 3400, 1706, 1669, 1571, 1490, 1458

NMR (DMSO-d$_6$, δ): 0.82–2.36

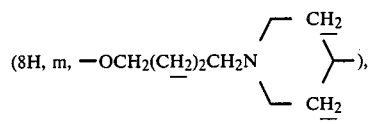

2.23 (3-H, s,—COCH$_3$), 2.58–3.76

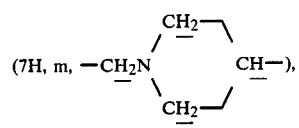

3.57 (3H, s, —OCH$_3$(P) ), 3.79–4.26 (2H, m, —OCH$_2$-), 3.89 (2H s, —COCH$_2$-), 6.03

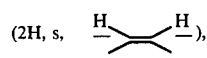

6.12 (1H, d, J=2.0Hz, C$_6$'—H), 6.26–7.36 (11H, m, C$_2$-H and aromatic H), 7.58–8.08 (1H, m, C$_4$-H)

EXAMPLE 4

3-Acetyl-2-[2-[3-[4-(4-fluorobenzoyl)-1-piperidyl]-propoxy]-5-nitrophenyl]benzothiazoline (compound 8)

To a solution of 3-acetyl-2-[2-(3-chloropropoxy)-5-nitrophenyl]benzothiazoline (3.93 g) in acetone (20 ml), sodium iodide (1.50 g) is added and the mixture is refluxed for 2 hours. After cooling to room temperature, the reaction mixture is concentrated in vacuo to remove acetone. To the residue, benzene (20 ml) and 4-(4-fluorobenzoyl)piperidine (4.20 g) are added and the mixture is refluxed for 9 hours.

After cooling to room temperature, chloroform (100 ml) is added to the reaction mixture. The mixture is washed with N hydrochloric acid, N sodium hydroxide solution and then saturated sodium chloride solution. The solution is dried over anhydrous magnesium sulfate and concentrated in vacuo.

The oily residue is purified by silica gel column chromatography to give 3.10 g (55%) of the titled compound.

mp 169°–172° C.

IR (KBr, cm$^{-1}$): 1665, 1588, 1508, 1489, 1460, 1449, 1376, 1330, 1262 NMR (DMSO-d$_6$, δ): 1.57–3.53

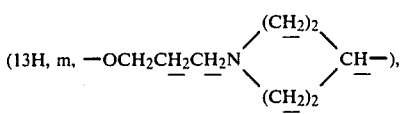

2.33 (3H, m, —COCH$_3$), 4.25 (2H, t, J=6.0 Hz, —OCH$_2$—), 6.83–8.30 (12H, m, C$_2$-H and aromatic H)

Following compounds can be prepared by the similar method as in the above examples.

3-Acetyl-2-[2-[4-[4-(4-fluorobenzoyl)-1-piperidyl]methoxy]-5-methoxyphenyl]benzothiazoline 3Acetyl-2-[2-[4-[4-(4-fluorobenzoyl)-1-piperidyl]-propoxy]-5-methoxyphenyl]benzothiazoline 3Acetyl-2-[2-[4-[4-(4-fluorobenzoyl)-1-piperidyl]hexyloxy]-5-methoxyphenyl]benzothiazoline 3Acetyl-2-[2-[4-[4-(4-fluorobenzylcarbonyl)-1-piperidyl]butoxy]-5-methoxyphenyl]benzothiazoline 3-Acetyl-2-[2-[4-[4-(4-fluoro-α-hydroxybenzyl)-1-piperidyl]-butoxy]-5-methoxyphenyl]benzothiazoline 3-Acetyl-2-[2-[4-[4-(4-fluorobenzoyl)-1-piperidyl]-butoxy]-phenyl]benzothiazoline 3-Acetyl-2-[2-[4-[4-(4-fluorobenzoyl)-1-piperidyl]-butoxy]-5-methylphenyl]benzothiazoline 3-Acetyl-2-[5-ethyl-2-[4-[4-(4-fluorobenzoyl)-1-piperidyl]-butoxy]phenyl]benzothiazoline 2-[2-[4-[4-(4-Fluorobenzoyl)-1-piperidyl]-butoxy]-5-methoxyphenyl]-3-propanoylbenzothiazoline 3-Acetyl-2-[2-[4-[4-(4-methoxybenzylcarbonyl)-1-pipreidyl]-butoxy]-5-methylphenyl]-benzothiazoline 3-Acetyl-2-[2-[4-[4-(4-methylbenzylcarbonyl)-1-piperidyl]-butoxy]-5-nitrophenyl]-benzothiazoline 3-Acetyl-2-[2-[4-[4-(α-hydroxy-4-methoxybenzyl)-1-piperidyl]-butoxy]-5-methylphenyl]-benzothiazoline 3-Acetyl-2-[2-[4-[4-(α-hydroxy-4-methylbenzoyl)-1-piperidyl]-butoxy]-5-nitrophenyl]-benzothiazoline Pharmacological Activities Calcium antagonists have not only beneficial effects in the treatment of many diseases but also serve as valuable research tools to elucidate excitation-contraction coupling in various muscle types (A. Fleckenstein, Ann. Rev. Pharmacol. 17, 149–166, 1977). Therefore, we examined the calciumantagonistic activity of the compounds of this invention.

Pharmacological test I

The action potentials on the smooth muscles of uterus, teania coli and portal vein depend on calcium ion, and therefore these smooth muscle preparations are useful for screening of calciumantagonists. We measured the calciumantagonistic activity of the compounds by the method using guineapig teania coli preparation.

Isolated guineapig teania coli was suspended in a 20 ml organ bath with Krebs solution at 32° C. and bubbled with 5% carbon dioxide in oxygen. After equilibration, the muscle was washed with $Ca^{++}$-free Krebs solution, and when the muscle had relaxed to basal level, it was suspended in $Ca^{++}$-free-high-K Krebs solution.

The muscle was exposed to the test compounds for 5 minutes before addition of $CaCl_2$, and the contraction evoked by $CaCl_2$ ($3\times10^{-4}M$) was recorded isotonically. The calciumantagonistic activity was represented by the concentration of the test compound which elicited 50% inhibition of $Ca^{++}$-evoked contraction ($IC_{50}$).

As shown in Table 1, the compounds of this invention had calciumantagonistic activity.

Blood platelet plays an important role only in hemostasis but also in thrombosis. Platelet hyperaggregability leads to an increase in the number of circulating platelet aggregates, which may contribute toward the development of cardiac arrhythmia, cardiac arrest or myocardial infarction. These cardiovascular diseases can be prevented by inhibition of platelet aggregation.

Therefore, we screened the influence of the test compounds on platelet aggregation in vitro, and found that they have antiaggregatory activity.

Pharmacological test II

Blood was obtained from an anesthetized rabbit using 0.1 volume of 3.8% sodium citrate as anticoagulant. Platelet rich plasma (PRP) was isolated by centrifugation at 650 rpm for 10 minutes at room temperature. After preincubation of PRP (0.25 ml) with various concentrations of the test compounds (14μl) for 1 minute at 37° C., collagen (3μg/ml: final concentration) or ADP (3μM: final concentration) was added to induce aggregation and the aggregation profiles were monitored by RIKADENKI six-channel aggregometer. The control experiment contained saline instead of the test compound.

The antiaggregatory activity was represented by the concentration of the test compounds which elicited 50% inhibition of the control response.

As shown in the Table 2, the compounds of this invention had antiaggregatory activity.

TABLE 1

| Calciumantagonistic activity | |
|---|---|
| compound No. | $IC_{50}$ [M] |
| 4 | $8.7 \times 10^{-6}$ |
| 5 | $8.2 \times 10^{-6}$ |
| 6 | $1.6 \times 10^{-6}$ |
| 7 | $3.2 \times 10^{-6}$ |

TABLE 2

| Antiaggregation activity | |
|---|---|
| compound No. | $IC_{50}$ [M] |
| 3 | $3.2 \times 10^{-6}$ |
| 4 | $3.2 \times 10^{-6}$ |
| 6 | $2.9 \times 10^{-7}$ |

The compounds can be administered either orally or parenterally. The dosage forms are tablet, capsule, granule, powder, suppository, injection, etc. The dose is adjusted depending on symptom, dosage form, etc., but usual daily dosage is 1 to 5000 mg, preferably 10 to 1000 mg, in one or a few divided doses.

Examples of formulation are shown below.

Example of formulation

| (a) Tablet | | |
|---|---|---|
| compound No. 6 | | 30 mg |
| lactose | | 150 mg |
| crystalline cellulose | | 50 mg |
| calcium carboxymethylcellulose | | 7 mg |
| magnesium stearate | | 3 mg |
| | total | 240 mg |
| compound No. 6 | | 50 mg |
| lactose | | 120 mg |
| crystalline cellulose | | 60 mg |
| calcium carboxymethylcellulose | | 7 mg |
| magnesium stearate | | 3 mg |
| | total | 240 mg |

The tablets may be treated with the common film-coating and further with sugar-coating.

| (b) Granule | | |
|---|---|---|
| compound No. 6 | | 30 mg |
| polyvinylpyrrolidone | | 25 mg |
| lactose | | 385 mg |
| hydroxypropylcellulose | | 50 mg |
| talc | | 10 mg |
| | total | 500 mg |
| (c) Powder | | |
| compound No. 6 | | 30 mg |
| lactose | | 500 mg |
| starch | | 440 mg |
| colloidal silica | | 30 mg |
| | total | 1000 mg |
| (d) Capsule | | |
| compound No. 6 | | 30 mg |

| | |
|---|---|
| lactose | 102 mg |
| crystalline cellulose | 56 mg |
| colloidal silica | 2 mg |
| total | 190 mg |

What we claim is:

1. A compound of the formula,

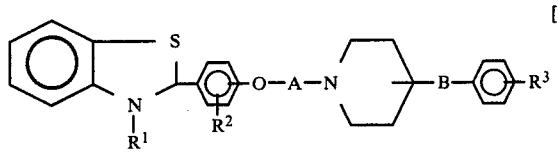

[I]

wherein
 $R^1$ is formyl or lower alkanoyl;
 $R^2$ is hydrogen, lower alkyl, lower alkoxy or nitro;
 $R^3$ is hydrogen, lower alkyl, lower alkoxy or halogen;
 A is lower alkylene;
 B is —CO—$(CH_2)_m$— or —CH(OH)—;
 m is 0 or 1; and
 when m is 0, $R^3$ is not hydrogen, or a non-toxic acid addition salt thereof.

2. The compound as in claim 1, wherein $R^1$ is acetyl.

3. The compound as in claim 1, wherein $R^2$ is methoxy or nitro.

4. The compound as in claim 1, wherein $R^3$ is hydrogen, methyl, methoxy, fluorine or chlorine.

5. The compound as in claim 1, wherein A is —(CH$_2$)$_3$— or —(CH$_2$)$_4$—.

6. A compound of the formula,

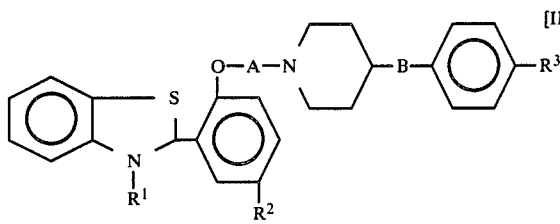

[II]

wherein
 $R^1$ is formyl or acetyl;
 $R^2$ is methoxy or nitro;
 $R^3$ is methyl, methoxy, chlorine or fluorine;
 A is —(CH$_2$)$_3$— or —(CH$_2$)$_4$—; and
 B is —CO—,
or a non-toxic acid addition salt thereof.

7. A compound of the formula,

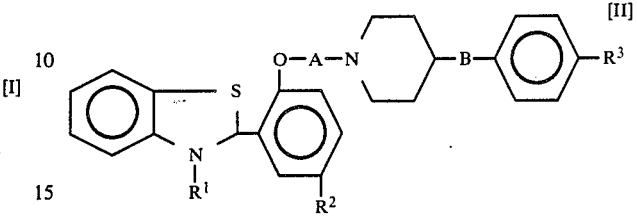

[II]

wherein
 $R^1$ is acetyl;
 $R^2$ is methoxy;
 $R^3$ is hydrogen;
 A is —(CH$_2$)$_4$—;
 B is —CO—$(CH_2)_m$— or —CH(OH)—; and m is 1, or a non-toxic acid addition salt thereof.

8. 3-Acetyl-2-[5-methoxy-2-[4-[4-(4-methoxybenzoyl)-1-piperidyl]butoxy]phenyl]benzothiazoline as in claim 6.

9. 3-Acetyl-2-[2-[4-[4-(4-chlorobenzoyl)-1-piperidyl]butoxy]-5-methoxyphenyl]benzothiazoline as in claim 6.

10. 3-Acetyl-2-[2-[4-[4-(4-fluorobenzoyl)-1-piperidyl]butoxy]-5-methoxyphenyl]benzothiazoline as in claim 6.

11. 3-Acetyl-2-[2-[4-[4-(α-hydroxyphenyl)-1-piperidyl]butoxy]-5-methoxyphenyl]benzothiazoline as in claim 7.

12. 3-Acety-2-[2-[4-(4-benzylcarbonyl-1-piperidyl)-butoxy]-5-methoxyphenyl]benzothiazoline as in claim 7.

13. A pharmaceutical composition comprising (i) a compound as in claim 1 in an amount sufficient for treatment for angina cordis, arrhythmia and thrombosis and (ii) at least one pharmaceutically acceptable excipient.

14. A method of treatment for angina cordis, arrhythmia and thrombosis which comprises administering a composition comprising a compound as in claim 1 and at least one pharmaceutically acceptable excipient.

* * * * *

UNITED STATES PATENT AND TRADEMARK OFFICE
CERTIFICATE OF CORRECTION

PATENT NO. : 4,547,513

DATED : October 15, 1985

INVENTOR(S) : Jun-ichi IWAO, et al

It is certified that error appears in the above-identified patent and that said Letters Patent is hereby corrected as shown below:

Column 4, line 20, change "the" (last instance) to --a--;

Column 4, line 22, a space should not appear between "1-" and "piperidyl]";

Column 4, line 58, after "3-acetyl" insert a dash;

Column 4, line 62, change "the" to --a--;

Column 7, line 1, change the first line thereof to read
--3-Acetyl-2-[2-[4-[4-(4-fluorobenzoyl)-1-piperidyl]- --;

Column 9, line 12, change "pipreidyl" to --piperidyl--;

Column 9, line 25, change "17" to --17--;

Column 9, line 43, change "muscule" to --muscle--.

Signed and Sealed this

Twentieth Day of May 1986

[SEAL]

Attest:

DONALD J. QUIGG

Attesting Officer

Commissioner of Patents and Trademarks